(12) United States Patent
Tsukada et al.

(10) Patent No.: US 6,649,142 B2
(45) Date of Patent: Nov. 18, 2003

(54) LABELED COMPOUNDS FOR MEASURING THE FUNCTION OF THE MUSCARINIC ACETYLCHOLINE NERVOUS SYSTEM

(75) Inventors: Hideo Tsukada, Hamamatsu (JP); Kengo Sato, Hamamatsu (JP); Shingo Nishiyama, Hamamatsu (JP); Norihiro Harada, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 0 days.

(21) Appl. No.: 10/258,061

(22) PCT Filed: Apr. 17, 2001

(86) PCT No.: PCT/JP01/03281

§ 371 (c)(1),
(2), (4) Date: Oct. 18, 2002

(87) PCT Pub. No.: WO01/79171

PCT Pub. Date: Oct. 25, 2001

(65) Prior Publication Data

US 2003/0113261 A1 Jun. 19, 2003

(30) Foreign Application Priority Data

Apr. 19, 2000 (JP) ........................................ 2000-118301

(51) Int. Cl.[7] ...................... A61K 51/00; A61K 101/00; A61K 123/00; C07D 211/42
(52) U.S. Cl. ...................... 424/1.81; 546/216; 424/9.44
(58) Field of Search ............................... 424/1.81, 9.44; 546/216

(56) References Cited

FOREIGN PATENT DOCUMENTS

JP 11-152270 6/1999

OTHER PUBLICATIONS

Kazuhiro Takahashi et al., "Synthesis and Autoradiographic Localization of Muscarinic Cholinergic Antagonist (+)N–[$^{11}$C]Methyl–3–Piperidyl Benzilate as a Potent Radioligand for Positron Emission Tomography", Applied Radiation and Isotopes, vol. 50, 1999, pp. 521–525.

Shanaz M. Tejani–Butt et al., "N–Substituted Derivatives of 4–Piperidinyl Benzilate: Affinities for Brain Muscarinic Acetylcholine Receptors", Life Sciences, vol. 47, No. 10, 1990, pp. 841–848.

Hirotaka Onoe et al., "Ketamine Increases the Striatal N–[$^{11}$C]methylspiperone Binding in Vivo: Positron Emission Tomography Study Using Conscious Rhesus Monkey", Brain Research 663, 1994, pp. 191–198.

*Primary Examiner*—Charanjit Aulakh
(74) *Attorney, Agent, or Firm*—Morgan, Lewis & Bockius LLP

(57) ABSTRACT

A muscarinic acetylcholine nervous system labeled compound for positron emission tomography measurement of the present invention has a structure represented by undermentioned general formula (I):

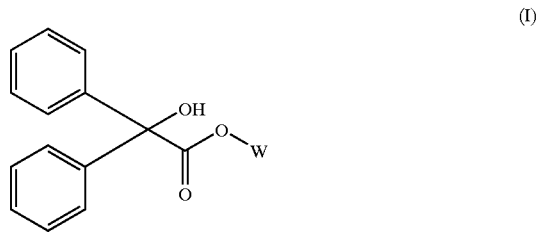

(I)

[in the formula, W represents one selected from the group consisting of groups represented by undermentioned formulae (II) and (III):

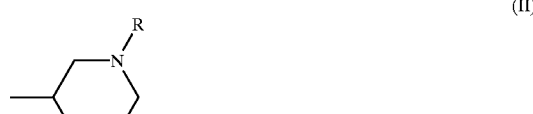

(II)

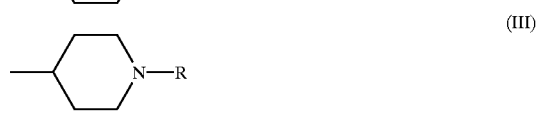

(III)

(in the formulae, R represents one selected from the group consisting of an $^{11}$C-labeled ethyl group and an $^{11}$C-labeled propyl group), and in the case that W is a group represented by above-mentioned formula (II), above-mentioned formula (I) is the (+)-isomer].

3 Claims, 8 Drawing Sheets

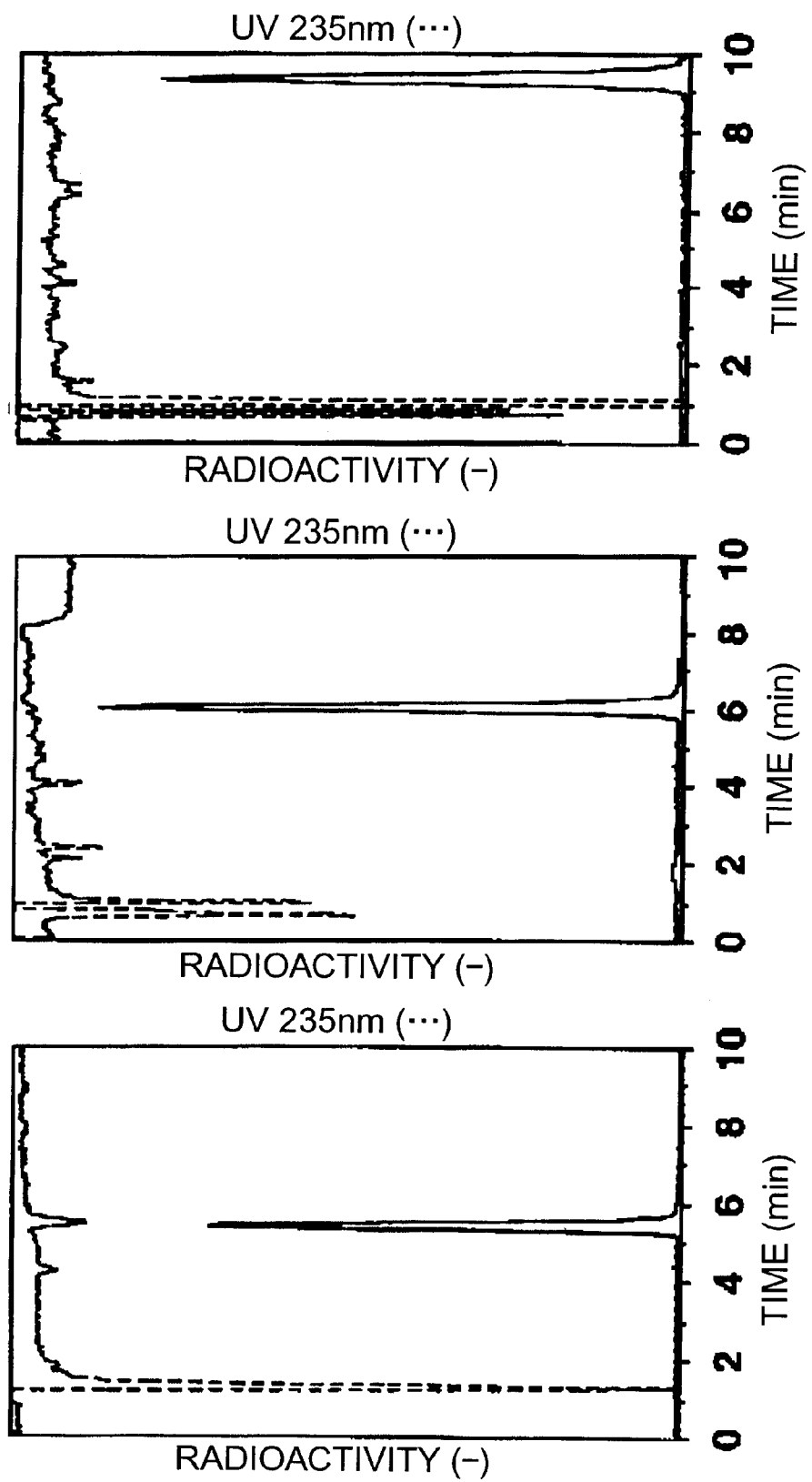

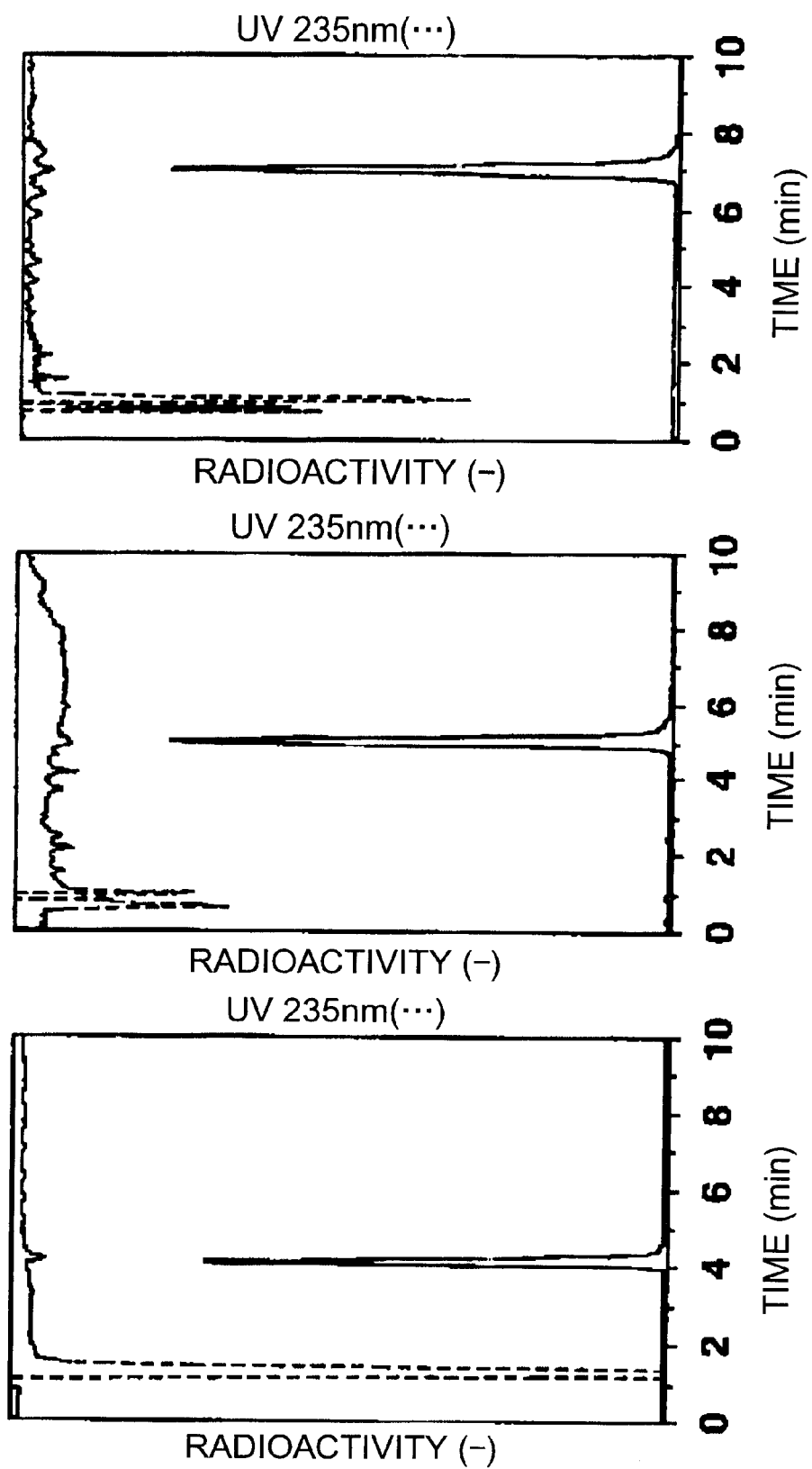

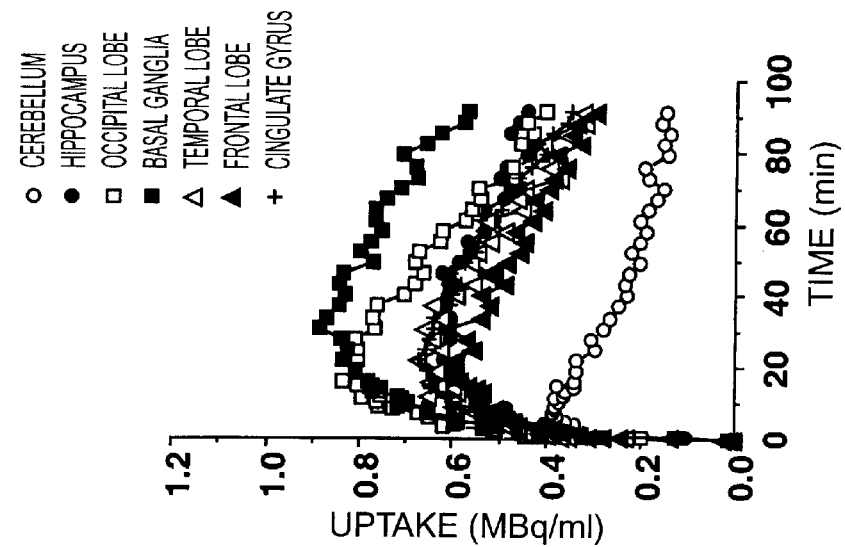

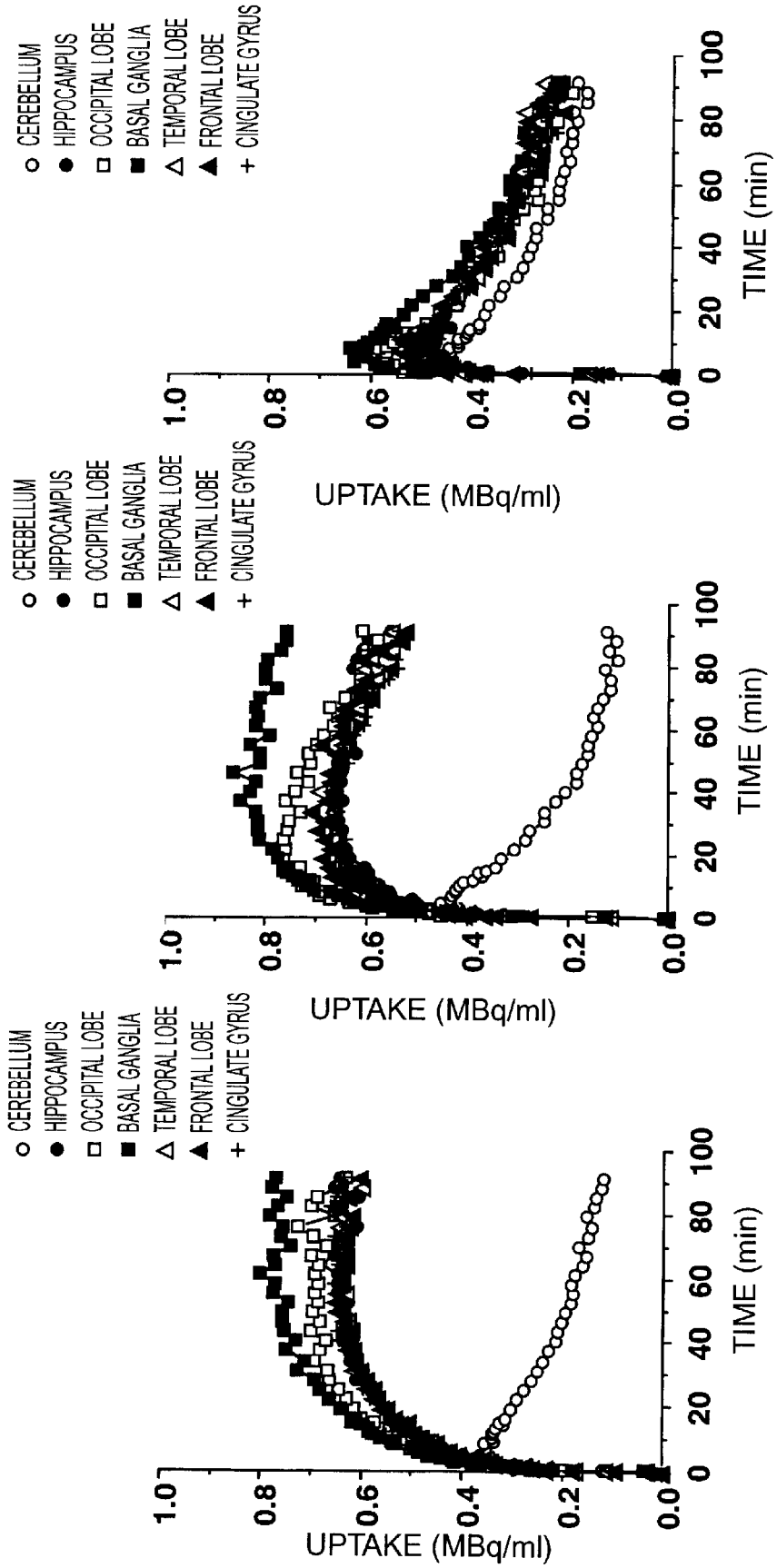

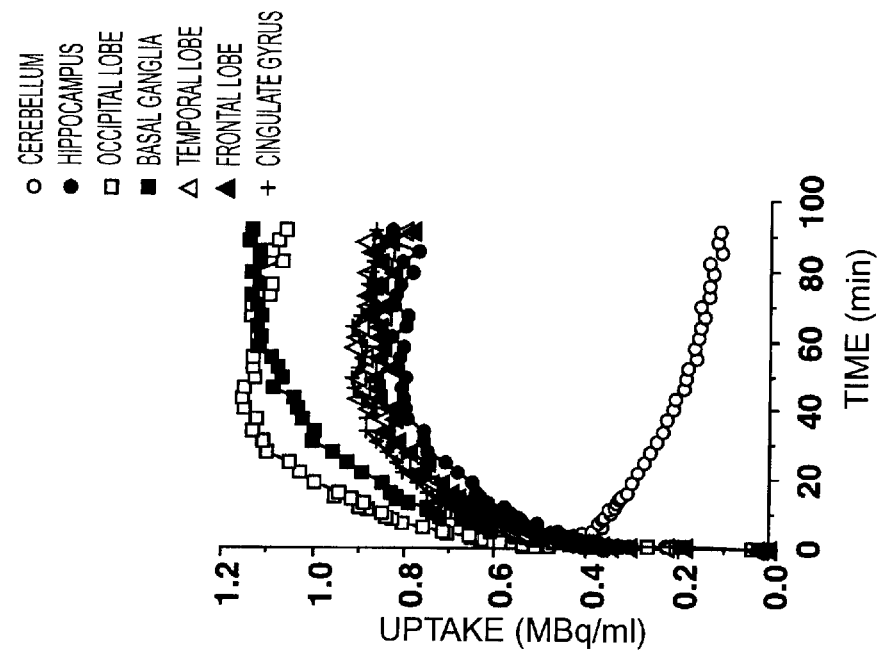
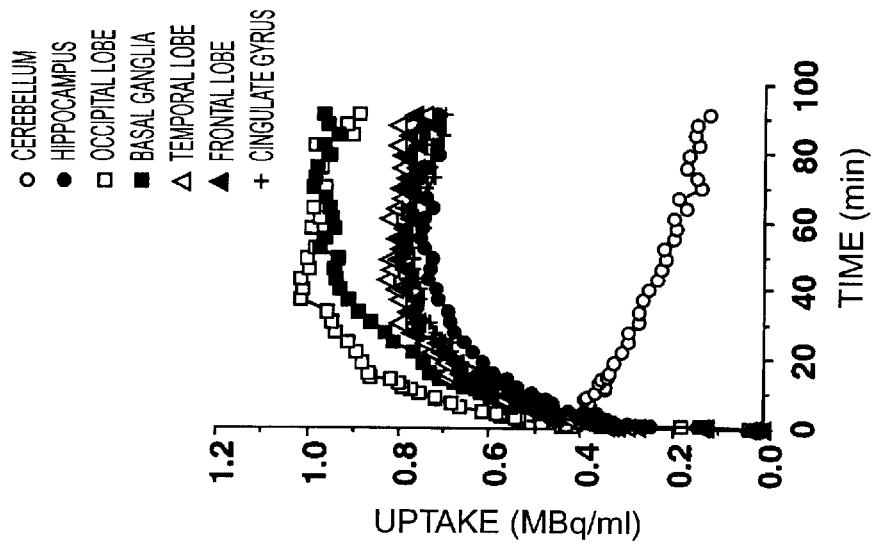
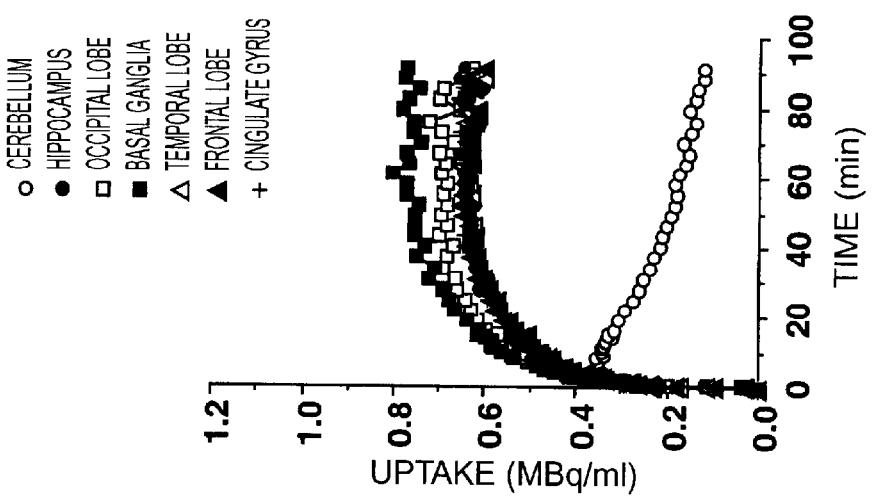

LABELED COMPOUNDS FOR MEASURING THE FUNCTION OF THE MUSCARINIC ACETYLCHOLINE NERVOUS SYSTEM

This application is a 371 of PCT/JP01/03281 filed Apr. 17, 2001, now WO 01/79171 Oct. 25, 2001.

DESCRIPTION

TECHNICAL FIELD

The present invention relates to a muscarinic acetylcholine nervous system labeled compound, and more specifically to a muscarinic acetylcholine nervous system labeled compound for positron emission tomography (PET) measurement.

BACKGROUND ART

With an aging society, the increasing economic burden due to an increase in the number of people with dementia is becoming a social problem, and hence elucidation of the condition of dementia and development of effective anti-dementia drugs are needed.

The pathology of dementia is not yet clear, but research hitherto has suggested that deterioration of the functioning of the acetylcholine nervous system is one cause of dementia. Evaluation of the functioning of the acetylcholine nervous system thus plays a very important role in elucidating the condition of dementia and in developing anti-dementia drugs, and hence there are strong calls for the development of non-intrusive methods of carrying out such evaluation and of labeled compounds suitable for use in these methods.

A method in which positron emission tomography (hereinafter referred to as 'PET') measurements are carried out using a labeled compound possessing a positron-emitting nuclear species is known as a non-intrusive method for evaluating the functioning of the acetylcholine nervous system. In this method, acetylcholine nervous system receptors are labeled using the labeled compound, and γ-rays that are emitted upon positrons emitted from the emitting nuclear species combining with matter-constituting electrons and annihilation taking place are measured, thus measuring the distribution of the receptors.

[$^{11}$C]N-methyl-4-piperidyl benzilate (hereinafter referred to as '[$^{11}$C]4-NMPB') has been proposed as a muscarinic acetylcholine nervous system labeled compound for use in such PET measurements. However, there have been problems such as the following with PET measurements using [$^{11}$C]4-NMPB:

(i) the ionicity of [$^{11}$C]4-NMPB is low in the blood, and hence the liposolubility is high, and thus the ability to migrate into tissue is good, but the amount of [$^{11}$C]4-NMPB that binds non-specifically to muscarinic acetylcholine nervous system receptors in the tissue is high, and hence errors are prone to arising when measuring the amount of [$^{11}$C]4-NMPB that binds specifically to the receptors;

(ii) [$^{11}$C]4-NMPB has a structure for which optical isomers do not exist, and hence errors are prone to arising when measuring the amount of [$^{11}$C]4-NMPB that binds specifically to muscarinic acetylcholine nervous system receptors;

(iii) the affinity of [$^{11}$C]4-NMPB to the receptors is high and the dissociation constant ($k_4$) is very low, and hence the movement of [$^{11}$C]4-NMPB in the brain is prone to being affected by changes in the local blood flow amount, and thus in the case of a disease model or a condition accompanied by a drop in cerebral circulation, it is difficult to distinguish whether measurement results are due to genuine changes in the activity of the muscarinic acetylcholine nervous system receptors or merely due to changes in the local blood flow amount in the brain;

(iv) the affinity of [$^{11}$C]4-NMPB to the muscarinic acetylcholine nervous system receptors is very high compared with that of acetylcholine, which is an intrinsic neurotransmitter, and hence it is difficult to measure competition on the receptors between acetylcholine that has been discharged from preganglionic nerves due to neurotransmission and the labeled compound.

Moving on, it is disclosed in Japanese Patent Application Laid-open No. 11-152270 that by using [$^{11}$C](±)N-methyl-3-piperidyl benzilate (hereinafter referred to as '[$^{11}$C](±)3-NMPB'), PET measurements can be carried out with higher precision than when [$^{11}$C]4-NMPB is used. However, even using [$^{11}$C](±)3-NMPB has still not been sufficient with regard to carrying out PET measurements with improved precision.

DISCLOSURE OF THE INVENTION

In view of the problems of the prior art described above, it is an object of the present invention to provide a muscarinic acetylcholine nervous system labeled compound that enables PET measurements to be carried out efficiently with improved precision and without there being influence from changes in the blood flow amount in the region of interest in the brain, a method of manufacturing the labeled compound, and a positron emission tomography measurement method using the labeled compound.

The present inventors carried out assiduous studies to attain the above object, and as a result discovered that the problems described above can be resolved by using an $^{11}$C-labeled benzilic acid alkylpiperidyl ester having a specific structure as a muscarinic acetylcholine nervous system labeled compound, thus arriving at the present invention.

Specifically, a muscarinic acetylcholine nervous system labeled compound for positron emission tomography measurement of the present invention is characterized by having a structure represented by undermentioned general formula (I):

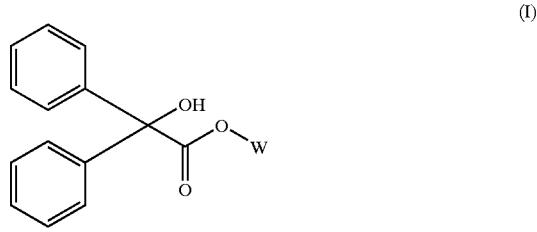

[in the formula, W represents one selected from the group consisting of groups represented by undermentioned formulae (II) and (III):

-continued

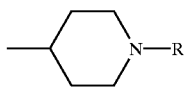
(III)

(in the formulae, R represents one selected from the group consisting of an $^{11}$C-labeled ethyl group and an $^{11}$C-labeled propyl group), and in the case that W is a group represented by above-mentioned formula (II), above-mentioned formula (I) is the (+)-isomer].

Moreover, a method of manufacturing a muscarinic acetylcholine nervous system labeled compound for positron emission tomography measurement of the present invention is characterized by comprising a step of obtaining a compound represented by undermentioned formula (I):

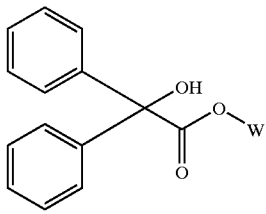
(I)

from an $^{11}$C-labeled alkyl halide represented by undermentioned formula (IV):

R—X (IV)

and a benzilic acid piperidyl ester represented by undermentioned formula (V):

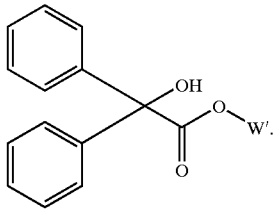
(V)

[In the formulae, R represents one selected from the group consisting of an $^{11}$C-labeled ethyl group and an $^{11}$C-labeled propyl group, X represents a halogen atom, W' represents one selected from the group consisting of a (+)3-piperidyl group and a 4-piperidyl group, and W represents one selected from the group consisting of groups represented by undermentioned formulae (II) and (III):

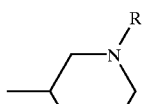
(II)

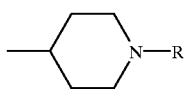
(III)

(in the formulae, R represents one selected from the group consisting of an $^{11}$C-labeled ethyl group and an $^{11}$C-labeled propyl group).]

Furthermore, a positron emission tomography measurement method of the present invention comprises: a step of administering the above-mentioned labeled compound of the present invention to a subject, thus labeling muscarinic acetylcholine nervous system receptors of the subject with the labeled compound; and a step of measuring γ-rays emitted through the combination of positrons emitted from an emitting nuclear species possessed by the labeled compound and prescribed matter-constituting electrons.

According to the present invention, by using a labeled compound represented by above-mentioned formula (I), in PET measurements, the amount of γ-rays corresponding to specific binding between the labeled compound and the above-mentioned receptors can be measured with high precision without there being influence from changes in the blood flow amount. It thus becomes possible to obtain information on the acetylcholine nervous system in prescribed regions of interest in the brain with high precision. Moreover, the affinity of the labeled compound of the present invention to the receptors is lower than that of conventional labeled compounds, and binding of the labeled compound to the receptors and dissociation of the labeled compound from the receptors occurs in a relatively short time, and hence PET measurements can be carried out efficiently.

BRIEF DESCRIPTION OF THE DRAWINGS

FIGS. 3A to 3C are graphs showing HPLC analysis results for labeled compounds obtained in Examples 1 and 2 and Comparative Example 1; in each graph the full line shows results of analysis in radioactive mode, and the broken line shows results of analysis in UV mode (wavelength 235 nm).

FIGS. 4A to 4C are graphs showing HPLC analysis results for labeled compounds obtained in Examples 3 and 4 and Comparative Example 2; in each graph the full line shows results of analysis in radioactive mode, and the broken line shows results of analysis in UV mode (wavelength 235 nm).

FIGS. 5A to 5C are graphs showing the relationship between measurement time and radioactivity concentration in regions of interest, obtained from PET measurements using [$^{11}$C](+)3-NMPB, [$^{11}$C](+)3-NEPB and [$^{11}$C](+)3-NPPB.

FIGS. 6A to 6C are graphs showing the relationship between measurement time and radioactivity concentration in regions of interest, obtained from PET measurements using [$^{11}$C]4-NMPB, [$^{11}$C]4-NEPB and [$^{11}$C]4-NPPB.

FIGS. 8A to 8C are graphs showing the relationship between measurement time and radioactivity concentration in regions of interest, obtained from PET measurements using [$^{11}$C]4-NMPB, for the cases of administering 0 μg/kg (no administration), 50 μg/kg and 250 μg/kg respectively of E2020 to a subject.

BEST MODES FOR CARRYING OUT THE INVENTION

Following is a detailed description of preferable embodiments of the present invention, with reference to the drawings in places.

A labeled compound of the present invention has a structure represented by undermentioned general formula (I):

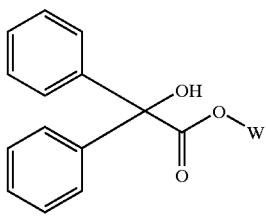

(I)

[in the formula, W represents one selected from the group consisting of groups represented by undermentioned formulae (II) and (III):

(II)

(III)

Figure 1A:
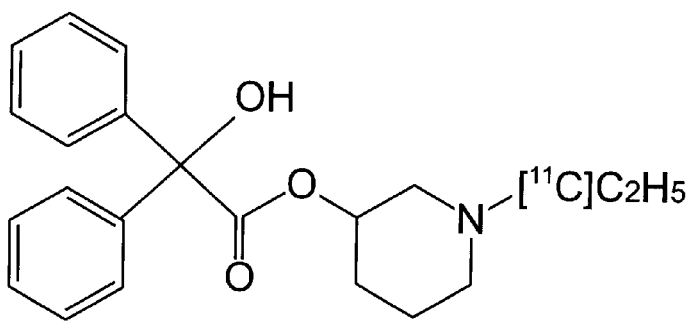
FIGS. 1A to 1D are explanatory drawings showing the structures of muscarinic acetylcholine nervous system labeled compounds of the present invention.
Figure 1B:
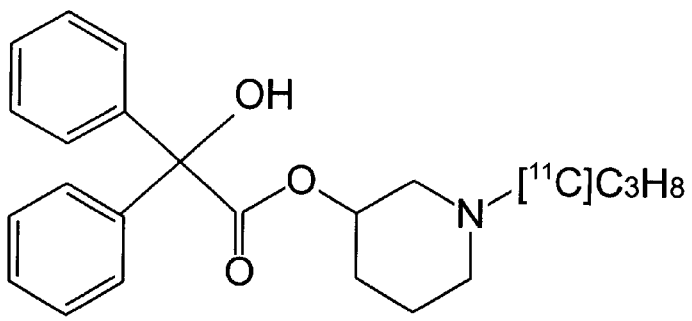
Figure 1C:
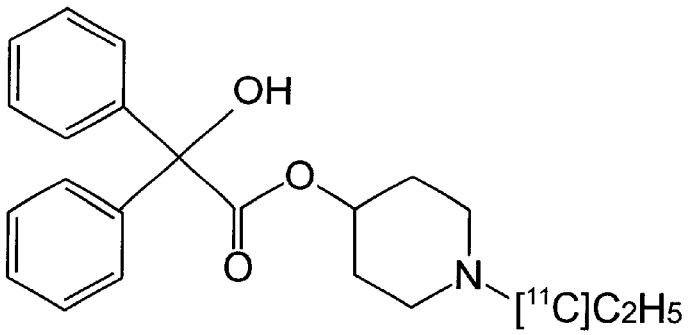
Figure 1D:
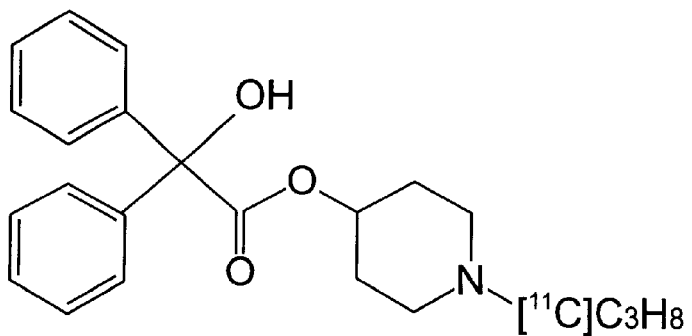

(in the formulae, R represents one selected from the group consisting of an $^{11}$C-labeled ethyl group and an $^{11}$C-labeled propyl group), and in the case that W is a group represented by above-mentioned formula (II), above-mentioned formula (I) is the (+)-isomer]; more specifically, labeled compounds of the present invention are:
[$^{11}$C](+)-N-ethyl-3-piperidyl benzilate (hereinafter referred to as '[$^{11}$C](+)3-NEPB') as shown in FIG. 1A;
[$^{11}$C](+)N-propyl-3-piperidyl benzilate (hereinafter referred to as '[$^{11}$C](+)3-NPPB') as shown in FIG. 1B;
[$^{11}$C]N-ethyl-4-piperidyl benzilate (hereinafter referred to as '[$^{11}$C]4-NEPB') as shown in FIG. 1C; and
[$^{11}$C]N-propyl-4-piperidyl benzilate (hereinafter referred to as '[$^{11}$C]4-NPPB') as shown in FIG. 1D.

Out of the groups represented by R in above-mentioned formulae (II) and (III), the $^{11}$C-labeled propyl group includes both an $^{11}$C-labeled n-propyl group and an $^{11}$C-labeled isopropyl group; nevertheless, an $^{11}$C-labeled n-propyl group is preferable, since in this case it tends to be that the target labeled compound can be obtained easily and reliably.

Moreover, the optical isomers [$^{11}$C](−)3-NEPB and [$^{11}$C](−)3-NPPB are present in [$^{11}$C](+)3-NEPB and [$^{11}$C](+)3-NPPB respectively; the (+)-isomers, which are the labeled compounds of the present invention, may be used in the form of a mixture with the respective (−)-isomer, i.e. in the form of [$^{11}$C](±)3-NEPB or [$^{11}$C](±)3-NPPB, or may be used after separating the (+)-isomer from the mixture. An example of a method of isolating the (+)-isomer from the mixture of optical isomers is optically resolving column chromatography using a column in which a polysaccharide derivative is supported on silica gel.

Moreover, [$^{11}$C](−)3-NEPB and [$^{11}$C](−)3-NPPB are not able to bind specifically to the above-mentioned receptors, and hence, for example, by carrying out PET measurements using [$^{11}$C](+)3-NEPB or [$^{11}$C](+)3-NPPB alone, and comparing with measurement results for the case that [$^{11}$C](−)

3-NEPB or [$^{11}$C](−)3-NPPB is used alone, it is possible to determine the amount of the labeled compound that is bound specifically to the receptors with improved precision.

Next, a description will be given of a method of manufacturing the compounds (I) of the present invention.

A compound (I) of the present invention can be obtained by the method represented by undermentioned reaction formula (A):

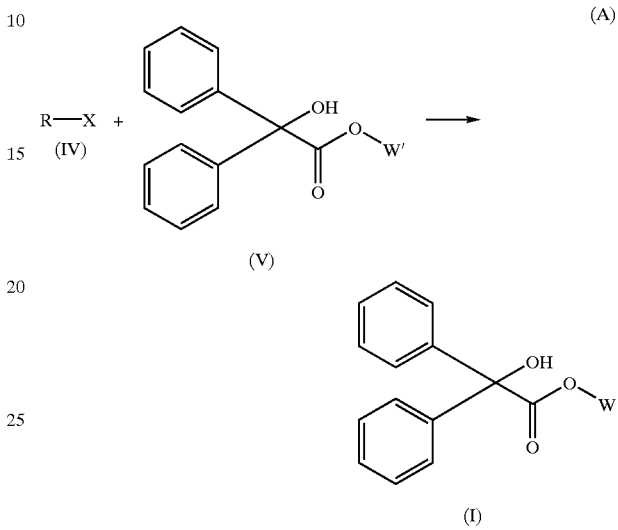

(A)

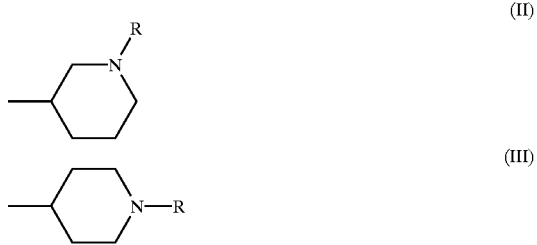

(I)

[in the formula, R represents one selected from the group consisting of an $^{11}$C-labeled ethyl group and an $^{11}$C-labeled propyl group, X represents a halogen atom, W' represents one selected from the group consisting of a (+)3-piperidyl group and a 4-piperidyl group, and W represents one selected from the group consisting of groups represented by undermentioned formulae (II) and (III):

(II)

(III)

(in the formulae, R represents one selected from the group consisting of an $^{11}$C-labeled ethyl group and an $^{11}$C-labeled propyl group), wherein in the case that W is a group represented by above-mentioned formula (II), above-mentioned formula (I) is the (+)-isomer, and in the case that W' is a (+)3-piperidyl group, W is a group represented by above-mentioned formula (II), whereas in the case that W' is a 4-piperidyl group, W is a group represented by above-mentioned formula (III)]; i.e. by reacting an $^{11}$C-labeled alkyl halide (IV) and a benzilic acid piperidyl ester (V) together. Here, examples of X (the halogen atom) in above-mentioned formula (IV) include a chlorine atom, a bromine atom and an iodine atom, with an iodine atom being preferable. If the halogen atom of the $^{11}$C-labeled alkyl halide (IV) is an iodine atom, then it tends to be possible to carry out the reaction easily and efficiently. Moreover, there are no particular limitations on the method or reaction conditions of the above reaction, with it being possible to use ones that have been publicly known from hitherto. For example, the target compound (I) can be obtained by carrying out the above reaction in a dimethylformamide (DMF) solvent with a reaction time of 3 to 6 minutes and a reaction temperature of 100° C. Furthermore, in the reaction, dimethylsulfoxide (DMSO) and so on can be used as the solvent instead of dimethylformamide (DMF). The identity of the compound (I) obtained through the reaction can be verified using column chromatography, nuclear magnetic resonance (NMR) absorption spectroscopy using an optically isomeric shift reagent, optical rotation angle measurement and so on.

There are no particular limitations on the method of synthesizing the $^{11}$C-labeled alkyl halide (IV) that is a starting material of the reaction represented by above-mentioned reaction formula (A); for example, an $^{11}$C-labeled alkyl iodide (IV-a) can be obtained by the method represented by undermentioned reaction formula (B):

(B)

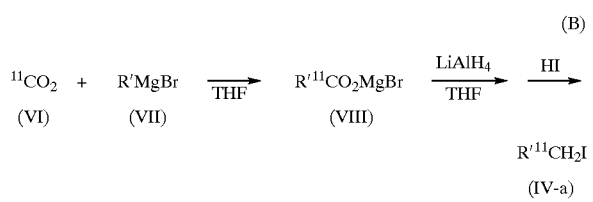

(in the formula, R' represents one selected from the group consisting of a methyl group and an ethyl group); i.e. by reacting $^{11}$C-labeled carbon dioxide (VI) and an alkyl magnesium bromide (VII) together, reducing the compound (VIII) thus obtained using a reducing agent such as LiAlH$_4$, and then treating with hydroiodic acid. In the above reaction, commercially sold $^{11}$C-labeled carbon dioxide may be used as the $^{11}$C-labeled carbon dioxide (VI), or $^{11}$C-labeled carbon dioxide synthesized using a method such as a $^{14}$N (p,α) $^{11}$C reaction may be used. Furthermore, regarding the alkyl magnesium bromide (VII) as well, either a commercially sold one or one synthesized using a method that has been publicly known since hitherto may be used.

Moreover, there are no particular limitations on the method of synthesizing the benzilic acid piperidyl ester (V) that is a starting material of the reaction represented by above-mentioned reaction formula (A); for example, the benzilic acid piperidyl ester (V) can be obtained by the method represented by undermentioned reaction formula (C):

(C)

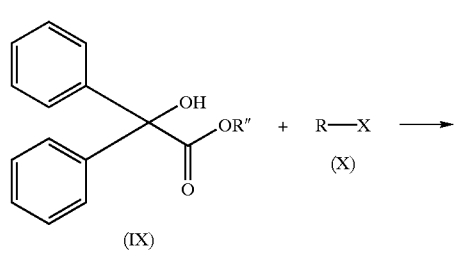

-continued

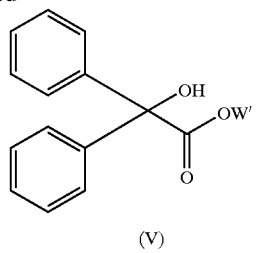

(V)

(in the formula, R" represents an alkyl group, and W' represents one selected from the group consisting of a 3-piperidyl group and a 4-piperidyl group); i.e. by reacting a benzilic acid ester (IX) and a piperidinol (X) together. Here, examples of the benzilic acid ester (IX) include methyl benzilate, ethyl benzilate, propyl benzilate and butyl benzilate. Moreover, in the case that the piperidinol (X) is 3-piperidinol, optical isomers exist; (+)3-piperidinol that has been isolated in advance by optical resolution may be used, or a mixture of the optical isomers (±)3-piperidinol may be used. In the case that (±)3-piperidinol is used, the (+)-isomer can be obtained by carrying out optical resolution using optically resolving column chromatography or the like after above-mentioned reaction (A) or (C).

By using a labeled compound of the present invention obtained in this way, in PET measurements, the amount of γ-rays corresponding to specific binding between the labeled compound and the above-mentioned receptors can be measured with high precision without there being influence from changes in the blood flow amount. It thus becomes possible to obtain information on the acetylcholine nervous system in prescribed regions of interest in the brain with high precision. Moreover, the affinity of the labeled compound of the present invention to the receptors is lower than that of conventional labeled compounds, and binding of the labeled compound to the receptors and dissociation of the labeled compound from the receptors occurs in a relatively short time, and hence PET measurements can be carried out efficiently.

There are no particular limitations on the PET measurement method in which the labeled compound of the present invention is used, with it being possible to carry out the PET measurements following a method that has been publicly known from hitherto (H. Onoe, O. Inoue, K. Suzuki, H. Tsukada, T. Itoh, N. Mataga and Y. Watanabe, Brain Research 663, 191–198 (1994)). Specifically, tomographic images are obtained of the brain of a subject such as a non-anesthetized rhesus monkey using a nuclear magnetic resonance tomographic imaging (MRI) apparatus, and regions of interest (ROIs) are determined based on the tomographic images. Next, the labeled compound of the present invention is administered to the subject from a vein thereof, and PET measurements are carried out on the regions of interest using a PET system. In the PET system, annihilation photons that are emitted through the combination of positrons emitted from an emitting nuclear species possessed by the labeled compound and matter-constituting electrons in the surroundings, i.e. γ-rays, are measured. Furthermore, if necessary the measurement data obtained can be processed using image reconstruction software to obtain images of the regions of interest. Here, from the standpoint of being able to distinguish fine details of the brain of the subject even in the case that the brain is small, it is preferable to use a combination of a PET system having excellent spatial resolution (e.g. SHR-7700made by Hamamatsu Photonics K.K.) and image reconstruction software (e.g. SHR Control II made by Hamamatsu Photonics K.K.).

EXAMPLES

Following is a more specific description of the present invention through examples and comparative examples; however, the present invention is not limited to the following examples.

Example 1

[$^{11}$C](+)N-ethyl-3-piperidyl benzilate (hereinafter referred to as '[$^{11}$C](+)3-NEPB') was synthesized following the procedure described below.

(Synthesis of $^{11}$C-labeled ethyl iodide ([$^{11}$C]ethyl iodide)

$^{11}$C-labeled carbon dioxide that had been manufactured through a $^{14}$N(p,α)$^{11}$C reaction using a cyclotron, Sumitomo Heavy Industries, Ltd., Cypris HM-18, and methyl magnesium bromide were reacted together, and the product obtained was reduced with lithium aluminum hydride and then treated with hydroiodic acid, thus obtaining $^{11}$C-labeled ethyl iodide. This synthesis was carried out using an automatic synthesis apparatus made by Sumitomo Heavy Industries, Ltd. The $^{11}$C-labeled ethyl iodide obtained was purified using gas chromatography (using a Chromosorb W HP 80/100 column made by GL Sciences Inc.).

Synthesis of (+)3-piperidyl benzilate ((+)3-PB)

30 ml of benzene, 0.4 g (4 mmol) of 3-piperidinol and 1.0 g (4 mmol) of methyl benzilate were put into a 50 ml 3-mouth flask equipped with a stirrer, a reflux condenser, and a molecular sieve 4A (15 g) tube and a soda lime tube for trapping methanol from out of the solvent that drips down through the reflux condensation, and the mixture was refluxed by heating while stirring. After all of the methyl benzilate had dissolved, 20 mg of sodium methoxide (made by Aldrich) was added to the solution and reaction was carried out for 3 hours. After the reaction had been completed, the reaction liquid was cooled to room temperature, and then 50 ml of 1N hydrochloric acid was added, and the organic solvent layer was removed. The aqueous solution layer obtained was washed twice with 50 ml of ether, and was then made basic using a 28% ammonium hydroxide aqueous solution. The aqueous solution was subjected to ether extraction, the ether layer obtained was washed twice with 50 ml of water, and then drying was carried out using anhydrous potassium carbonate. After removing the drying agent, the solvent was evaporated off under reduced pressure, thus obtaining an oily residue, and then this residue was recrystallized from ether-hexane, thus obtaining 0.5 g of (±)3-piperidyl benzilate ((±)3-PB) as crystals (yield 40%).

The structure of the compound obtained was verified using $^1$H-NMR and mass spectrometry.

$^1$H-NMR (δ, ppm): 7.36 (m, 10H), 4.92 (m, 1H), 2.94 (m, 1H), 2.70 (m, 4H), 1.82 (m, 1H), 1.71 (m, 1H), 1.47 (m, 2H), 1.26 (m, 4H)

Mass spectrometry: (m/z (relative intensity)): 312 (0.16), 183 (35.5), 105 (45.1), 83 (100), 77 (30.0)

The compound was subjected to optical resolution using the following HPLC system (A).

HPLC System (A)
Column: Daiseru Chemicals Chiralcel OJ column (4.6×250 mm)
Solvent: Hexane/ethanol mixed solvent (mixing ratio:80/20, v/v)
Flow rate: 0.5 ml/min Synthesis of [$^{11}$C](+)N-ethyl-3-piperidyl benzilate ([$^{11}$C](+)3-NEPB)

The $^{11}$C-labeled ethyl iodide was trapped at −40° C. in a 2 ml reaction vial into which had been placed 0.5 mg of the (+)3-PB that had been dissolved in 200 μl of DMF, this being in a helium stream (150 ml/min) through $P_2O_5$ and a soda lime trap. Once the amount of radiation had reached a maximum, the vial was heated at 100° C. for 3 minutes. The vial was then cooled, and the reaction mixture was purified using the following HPLC system.

HPLC System (B)
Column: MegaPak SIL C18-10 column made by JASCO Corporation (7.8×300 mm)
Solvent: Acetonitrile/30 mM ammonium acetate/acetic acid mixed solution (400/600/2, v/v/v)
Flow rate: 6 ml/min The solvent was removed from the fraction obtained in this way, and then the residue was dissolved in 10 ml of physiological saline, and filtering was carried out through a 0.22 μm sterilization filter into a 10 ml multi-dose vial, thus obtaining the target compound. The yield of the compound obtained based on the $^{11}$C-labeled alkyl iodide, the radioactivity yield, the specific radioactivity and the radiochemical purity were measured using the HPLC system (B) described above and the following HPLC system (C).

HPLC System (C)
Column: FinePak SIL C18S column made by JASCO Corporation (4.6×50 mm)
Solvent: Acetonitrile/ammonium acetate/acetic acid mixed solution (500/500/1, v/v/v)
Flow rate: 2 ml/min

Example 2

[$^{11}$C](+)N-propyl-3-piperidyl benzilate ([$^{11}$C](+)3-NPPB) was synthesized following the procedure described below.

Synthesis of $^{11}$C-labeled propyl iodide ([$^{11}$C]propyl iodide)

$^{11}$C-labeled carbon dioxide that had been manufactured through a $^{14}$N (p,α)$^{11}$C reaction using a cyclotron, Sumitomo Heavy Industries, Ltd., Cypris HM-18, and ethyl magnesium bromide were reacted together, and the product obtained was reduced with lithium aluminum hydride and then treated with hydroiodic acid, thus obtaining $^{11}$C-labeled propyl iodide. This synthesis was carried out using an automatic synthesis apparatus made by Sumitomo Heavy Industries, Ltd.

Synthesis of [$^{11}$C](+)N-propyl-3-piperidyl benzilate ([$^{11}$C](+)3-NPPB)

The [$^{11}$C](+)N-propyl-3-piperidyl benzilate was synthesized as in Example 1, except that the $^{11}$C-labeled propyl iodide obtained through the synthesis described above was used instead of $^{11}$C-labeled ethyl iodide. The yield based on the $^{11}$C-labeled alkyl iodide, the radioactivity yield, the specific radioactivity and the radiochemical purity were measured for the compound obtained as in Example 1.

Example 3

[$^{11}$C]N-ethyl-4-piperidyl benzilate ([$^{11}$C]4-NEPB) was synthesized following the procedure described below.

Synthesis of 4-piperidyl benzilate 4-piperidyl benzilate was obtained as in Example 1, except that 4-piperidinol was used instead of 3-piperidinol. Note, however, that because optical isomers do not exist for the compound obtained, the optical resolution of Example 1 was not carried out.

Synthesis of [$^{11}$C]N-ethyl-4-piperidyl benzilate

The [$^{11}$C]N-ethyl-4-piperidyl benzilate was synthesized as in Example 1, except that the 4-piperidyl benzilate obtained through the synthesis described above was used instead of (+)3-piperidyl benzilate. The yield based on the 11C-labeled alkyl iodide, the radioactivity yield, the specific radioactivity and the radiochemical purity were measured for the compound obtained as in Example 1.

Example 4

Synthesis of [11C]N-propyl-4-piperidyl benzilate

The [11C]N-propyl-4-piperidyl benzilate was synthesized as in Example 1, except that the 11C-labeled propyl iodide obtained in Example 2 was used instead of 11C-labeled ethyl iodide, and the 4-piperidyl benzilate obtained in Example 3 was used instead of (+)3-piperidyl benzilate. The yield based on the 11C-labeled alkyl iodide, the radioactivity yield, the specific radioactivity and the radiochemical purity were measured for the compound obtained as in Example 1.

Comparative Example 1

Synthesis of [11C](+)N-methyl-3-piperidyl benzilate

[11C](+)N-methyl-3-piperidyl benzilate was synthesized as in Example 1, except that 11C-labeled methyl iodide was used instead of 11C-labeled ethyl iodide. The yield based on the 11C-labeled alkyl iodide, the radioactivity yield, the specific radioactivity and the radiochemical purity were measured for the compound obtained as in Example 1, except that an acetonitrile/0.1M ammonium acetate/acetic acid mixed solution (500/500/5, v/v/v) was used as the solvent in the HPLC system.

Comparative Example 2

Synthesis of [11C]N-methyl-4-piperidyl benzilate

[11C]N-methyl-4-piperidyl benzilate was synthesized as in Example 1, except that 11C-labeled methyl iodide was used instead of 11C-labeled ethyl iodide, and 4-piperidyl benzilate was used instead of (+)3-piperidyl benzilate. The yield based on the 11C-labeled alkyl iodide, the radioactivity yield, the specific radioactivity and the radiochemical purity were measured for the compound obtained as in Example 1.

For each of the compounds of Examples 1 to 4 and Comparative Examples 1 and 2 obtained as described above, the retention time in the separating column of HPLC system (B), the retention time in the analyzing column of HPLC system (C), the yield based on the 11C-labeled alkyl iodide, the radioactivity yield, the specific radioactivity and the radiochemical purity are shown in Table 1. Moreover, the results of the HPLC analysis on the 11C-labeled alkyl iodides and final products obtained in the examples and comparative examples are shown in FIGS. 2A to 2E, FIGS. 3A to 3C and FIGS. 4A to 4C.

Figure 2A:
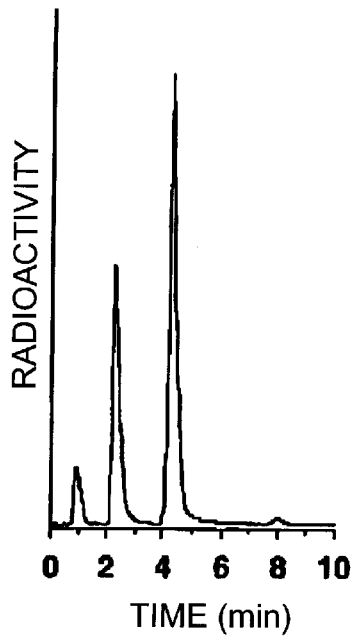
FIGS. 2A to 2E are graphs showing HPLC analysis results for $^{11}$C-labeled alkyl iodides obtained in Examples 1 to 4 and Comparative Examples 1 and 2.
Figure 2B:
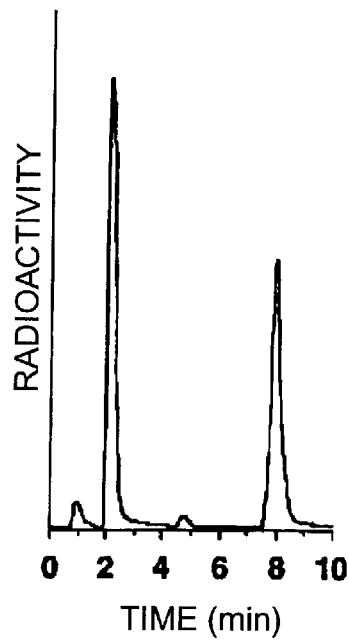
Figure 2C:
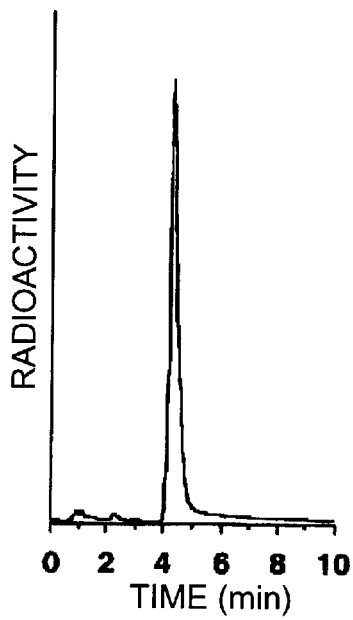
Figure 2D:
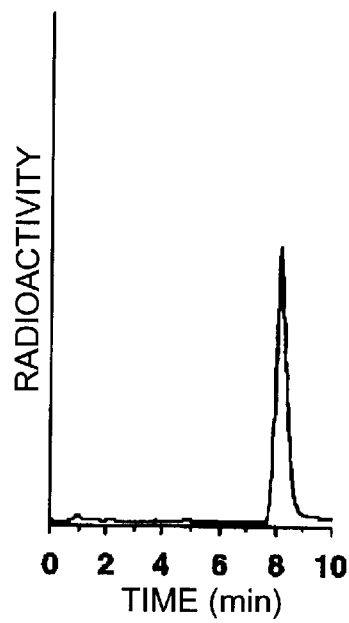
Figure 2E:
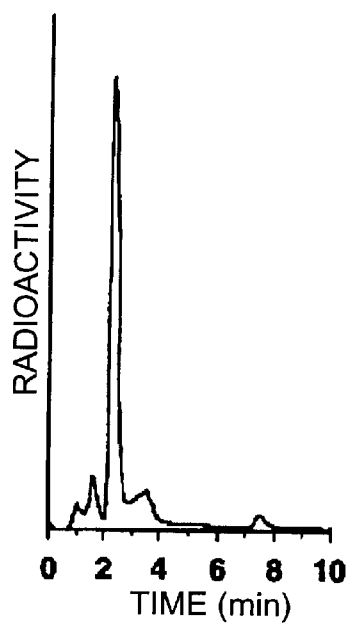

FIGS. 2A to 2E are graphs showing the HPLC analysis results for the 11C-labeled alkyl iodides; FIG. 2A was obtained from measurements on the 11C-labeled ethyl iodide before separation by gas chromatography, FIG. 2B from measurements on the 11C-labeled ethyl iodide after separation by gas chromatography, FIG. 2C from measurements on the 11C-labeled propyl iodide before separation by gas chromatography, FIG. 2D from measurements on the 11C-labeled propyl iodide after separation by gas chromatography, and FIG. 2E from measurements on 11C-labeled methyl iodide.

FIGS. 3A to 3C are graphs showing the HPLC analysis results for the final products obtained in Examples 1 and 2 and Comparative Example 1; FIG. 3A was obtained from measurements on [11C](±)3-NMPB, FIG. 3B from measurements on [11C](±)3-NEPB, and FIG. 3C from measurements on [11C](±)3-NPPB.

FIGS. 4A to 4C are graphs showing the HPLC analysis results for the final products obtained in Examples 3 and 4 and Comparative Example 2; FIG. 4A was obtained from measurements on [11C]4-NMPB, FIG. 4B from measurements on [11C]4-NEPB, and FIG. 4C from measurements on [11C]4-NPPB.

TABLE 1

| | | Retention time (min) | | Radioactivity | Specific | Radiochemical |
| | Compound | Separating column | Analyzing column | Yield (%) | yield (MBq) | radioactivity (GBq/mol) | purity (%) |
|---|---|---|---|---|---|---|---|
| Example 1 | [11C](+)3-NEPB | 12.8 | 6.5 | 38 | 309 | 66.3 | >99 |
| Example 2 | [11C](+)3-NPPB | 14.6 | 8.9 | 32 | 395 | 34.1 | >99 |
| Example 3 | [11C]4-NEPB | 9.9 | 5.0 | 42 | 336 | 337 | >99 |
| Example 4 | [11C]4-NPPB | 11.1 | 7.0 | 35 | 337 | 52.6 | >99 |
| Comparative Example 1 | [11C](+)3-NMPB | (7.1) | 5.4 | 70 | 2710 | 67.4 | >99 |
| Comparative Example 2 | [11C]4-NMPB | (5.5) | 4.1 | 59 | 1630 | 48.0 | >99 |

Next, PET measurements were carried out using the compounds obtained in Examples 1 to 4 and Comparative Examples 1 and 2 following the method described in the undermentioned document:

H. Onoe, O. Inoue, K. Suzuki, H. Tsukada, T. Itoh, N. Mataga and Y. Watanabe, Brain Research 663, 191–198 (1994)

First, a subject, a non-anesthetized rhesus monkey of body weight approximately 5 kg, was fastened to the PET apparatus (SHR-7700 made by Hamamatsu Photonics K.K.), and the transmission was measured for absorptive correction of the PET measurements. Approximately 200 MBq of the compound of one of Examples 1 to 4 and Comparative Examples 1 and 2 was then administered to the subject from a vein thereof, and dynamic measurements were carried out for 91 minutes. Moreover, for each set of measurements, measurements were carried out in advance on the subject using a nuclear magnetic resonance tomographic imaging (MRI) apparatus to obtain tomographic images, and the positions of the cerebellum, the hippocampus, the occipital lobe, the basal ganglia (striatum), the temporal lobe, the frontal lobe and the cingulate gyrus were determined based on the tomographic images; changes in the amount of γ-rays over time were measured for each of these regions of interest. The results are shown in FIGS. 5A to 5C and FIGS. 6A to 6C.

FIGS. 5A to 5C are graphs showing the relationship between time and radioactivity concentration for each of the regions of interest, with FIG. 5A being for the case that [11C](+)3-NMPB was used, FIG. 5B being for the case that [11C](+)3-NEPB was used, and FIG. 5C being for the case that [11C](+)3-NPPB was used.

FIGS. 6A to 6C are graphs showing the relationship between time and radioactivity concentration for each of the regions of interest, with FIG. 6A being for the case that [¹¹C]4-NMPB was used, FIG. 6B being for the case that [¹¹C]4-NEPB was used, and FIG. 6C being for the case that [¹¹C]4-NPPB was used.

As shown in FIGS. 5B, 5C, 6B and 6C, in the case that a compound of the present invention was used, the results obtained were that the radioactivity concentration corresponding to the distribution of the labeled compound in the basal ganglia and the occipital lobe was high, and moreover the radioactivity concentration was also relatively high for the frontal lobe and the temporal lobe. These results agree extremely well with the distribution of acetylcholine nervous system muscarinic receptors that has been known from hitherto, and hence it was verified that the compounds of the present invention are able to bind specifically to these receptors. Note that the reason that the absolute value of the uptake of the compounds of the present invention into the brain is low compared with the compounds of the comparative examples is that the compounds of the present invention have a low liposolubility. Carrying out a comparison using the value of the uptake of the labeled compound in each region of interest relative to the uptake in the cerebellum, higher values were obtained in the case that the compounds of the present invention were used.

Moreover, as is clear from comparing FIGS. 5B, 5C, 6B and 6C, which show the results for the cases that compounds of the present invention were used, with FIGS. 5A and 6A, which show the results for the cases that conventional labeled compounds were used, it was verified that the compounds of the present invention have a lower affinity to the brain, and binding and dissociation between the compounds of the present invention and the receptors occur in a relatively short time.

Next, PET measurements were carried out using the [¹¹C](+)3-NPPB obtained in Example 2 and the [¹¹C]4-NMPB obtained in Comparative Example 2 using the method described above, except that an intrinsic acetylcholine decomposition enzyme inhibitor E2020 (Aricept) was administered to the subject in advance. Upon being administered to a subject, E2020 has a function of increasing the amount of acetylcholine in the synaptic clefts and increasing the blood flow amount in the brain; by carrying out PET measurements using this drug, the dependence of the labeled compound on the blood flow amount in the brain can be evaluated.

Figure 7A:
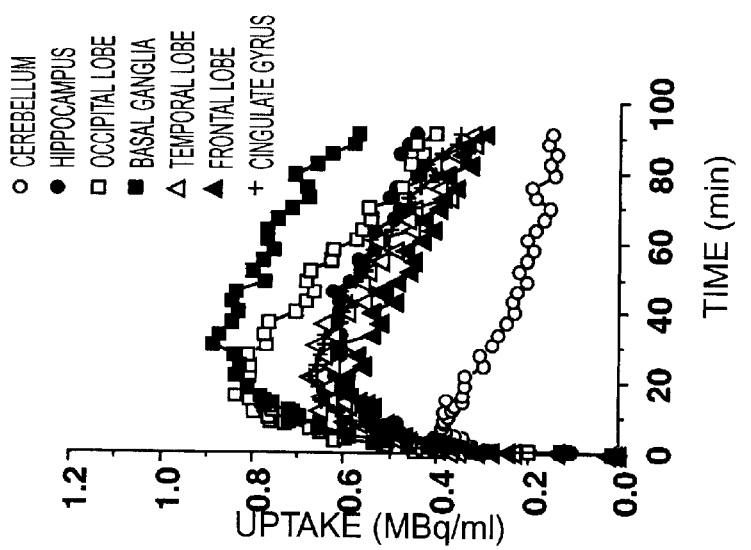
FIGS. 7A to 7C are graphs showing the relationship between measurement time and radioactivity concentration in regions of interest, obtained from PET measurements using [$^{11}$C](+)3-NPPB, for the cases of administering 0 μg/kg (no administration), 50 μg/kg and 250 μg/kg respectively of E2020 to a subject.
Figure 7B:
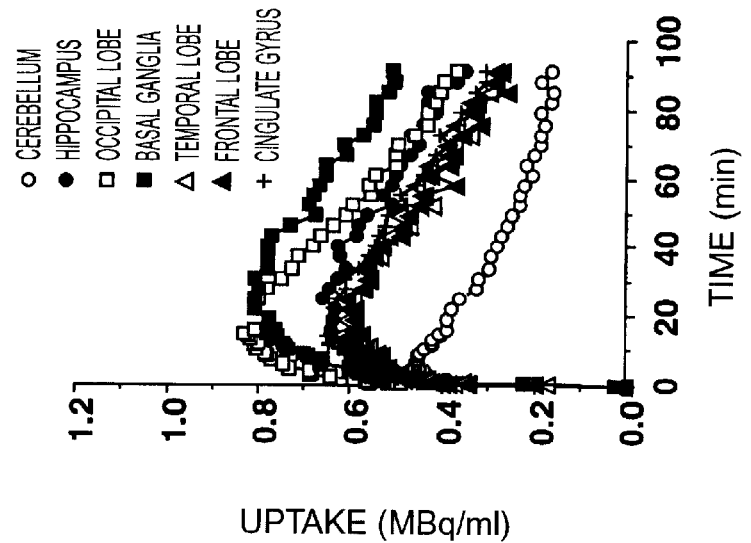
Figure 7C:
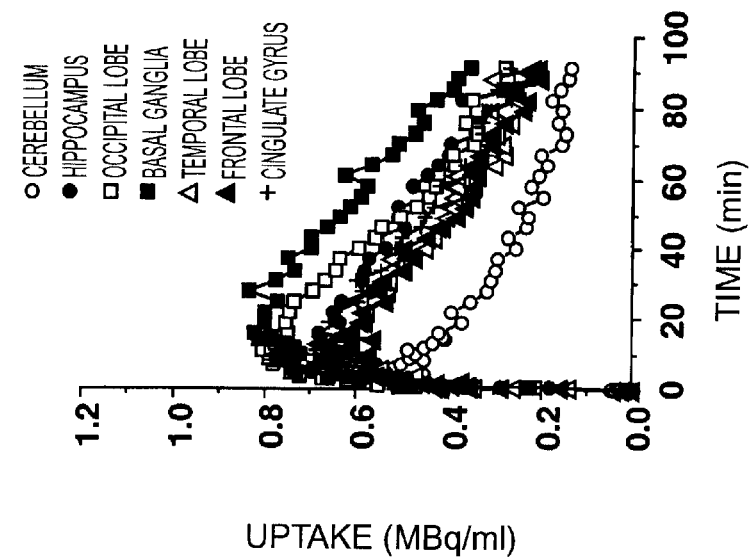

FIGS. 7A to 7C are graphs showing the relationship between measurement time and radioactivity concentration obtained from PET measurements using the [¹¹C](+)3-NPPB; FIG. 7A shows the case that E2020 was not administered, FIG. 7B the case that 50 μg/kg of E2020 was administered, and FIG. 7C the case that 250 μg/kg of E2020 was administered.

Moreover, FIGS. 8A to 8C are graphs showing the relationship between measurement time and radioactivity concentration for each of the regions of interest obtained from PET measurements using the [¹¹C]4-NMPB; FIG. 8A shows the case that E2020 was not administered, FIG. 8B the case that 50 μg/kg of E2020 was administered, and FIG. 8C the case that 250 μg/kg of E2020 was administered.

In the case that the [¹¹C]4-NMPB was used, it was found that there was an increase in the uptake of the labeled compound into the brain upon an increase in the blood flow amount. On the other hand, in the case that the [¹¹C]4-NPPB was used, influence due to an increase in the blood flow amount in the brain was not found. Moreover, in the case that the [¹¹C]4-NPPB was used, it was found that the rate of dissociation of the [¹¹C]4-NPPB from the receptors increased upon an increase in the amount of E2020 administered, and that competition in binding to the receptors occurred between intrinsic acetylcholine and the [¹¹C] 4-NPPB.

Industraial Applicability

As described above, according to the present invention it is possible to obtain a muscarinic acetylcholine nervous system labeled compound that enables PET measurements to be carried out efficiently with improved precision and without there being influence from changes in the blood flow amount in the region of interest.

What is claimed is:

1. A compound for labeling muscarinic acetyicholine receptors in the central nervous system for positron emission tomography measurement, wherein the compound is represented by the following general formula (I):

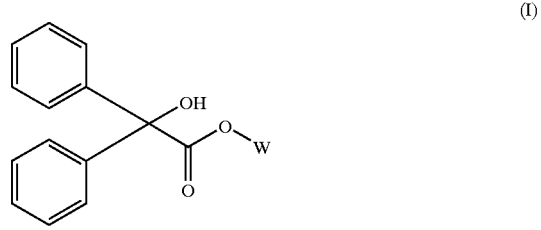

(I)

where W is one of the groups represented by the following formulae (II) and (III):

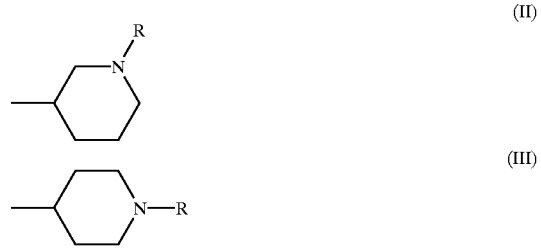

(II)

(III)

where R is a ¹¹C-labeled ethyl group or a ¹¹C-labeled propyl group, such that when W is a group represented by formula (II), then formula (I) is the (+)-isomer.

2. A process for preparing a compound of formula (I) as claimed in claim 1, comprising the step of reacting a ¹¹C-labeled alkyl halide represented by the following formula (IV):

R—X                                                                    (IV)

with a benzilic acid piperidyl ester represented by the following formula (V):

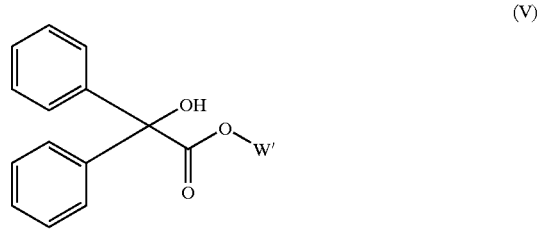

(V)

where R is a ¹¹C-labeled ethyl group or a ¹¹C-labeled propyl group, X is a halogen atom, and W' is a (+)-3-piperidyl group or a 4-piperidyl group.

3. A positron emission tomography measurement method, comprising the steps of:

administering the labeled compound according to claim 1 to a subject, thus labeling muscarinic acetylcholine receptors in the central nervous system of the subject with the labeled compound; and measuring γ-rays emitted through the combination of positrons emitted from an emitting nuclear species possessed by the labeled compound and matter-constituting electrons.

* * * * *